United States Patent [19]
Bui-Khac

[11] Patent Number: 5,981,254
[45] Date of Patent: Nov. 9, 1999

[54] PROCESS FOR PRODUCING THROMBIN FROM PLASMA

[75] Inventor: Trung Bui-Khac, Montreal, Canada

[73] Assignee: Haemacure Corporation, Quebec, Canada

[21] Appl. No.: 08/960,660

[22] Filed: Oct. 30, 1997

[51] Int. Cl.[6] .............................. C12N 9/74; A61K 35/14
[52] U.S. Cl. ......................... 435/214; 530/381; 530/384
[58] Field of Search .................................... 530/384, 381; 435/2, 214

[56] References Cited

U.S. PATENT DOCUMENTS

| | | |
|---|---|---|
| 5,143,838 | 9/1992 | Kraus et al. . |
| 5,290,918 | 3/1994 | Bui-Khac . |
| 5,304,372 | 4/1994 | Michalski et al. . |
| 5,506,127 | 4/1996 | Proba et al. . |

OTHER PUBLICATIONS

Morris & Morris, Separation Methods in Biochemistry, Second Ed., Pitman Publishing, 1976, pp. 300–303.

Ahern, T.J. & A.M. Klibanov, (1985). The Mechanism of Irreversible Enzyme Inactivation at 100° C; Science, 228:1280–1284.

Burnout, T. & M. Burnouf–Radosevich (1993) "Strategy of Virus Removal/Inactivation of Plasma–Derived Products: Interest of Nanofiltration. . . "; JAACT Proceedings, Manuscript supplied by T. Burnouf.

Dietrich, S.L., et al. (1990) "Transmission of Human Immunodeficiency Virus Type 1 by Dry–Heated Clotting Factor Concentrates"; Vox Sang; 59:129–135.

Harbour, C., et. al. (1991) "Viral Contamination of Therapeutic Proteins: a Challenge for Downstream Processing"; Australian Journal of Biotechnology. 5(2):81–86.

Heimburger, N. & H.E. Karges (1989) "Strategies to Produce Virus–Safe Blood Derviratives"; Virus Inactivation in Plasma Products; Curr Stud Hematol Blood Transfus; Morgenthaler J–J (ed): No. 56, pp. 23–33.

Horowitz, B. (1989) "Investigations into the Application of Tri(n–Buryl)Phosphate/Detergent Mixtures to Blood Derivatives"; Morgenthaler J–J (ed): Virus Inactivation in Plasma Products; Curr Stud Hematol Blood Transfus; Basel, Karger, 1989, No. 56, pp. 83–96.

Kuhnl, P. et al. (1989) "Reduction of Virus Load in Blood Donations by Screening Methods"; Morgenthaler J–J (ed): Virus Inactivation in Plasma Products; Curr Stud Hematol Blood Transfus; Basel, Karger, 1989, No. 56, pp. 9–22.

Loomis, E.C. & W.H. Seegers (1944) "Purified Prothrombin: Factors which Influence Its Activation", pp. 265–271.

Manabe S. (1992) "Virus Removal and Inactivation in Process Validation"; Animal Cell Technology: Basics & Applied Aspects (Murakami, H. Shirahata, S. Tachibana, H., eds.), pp. 15–30.

Miletich, J.P. et al., (1980) The Synthesis of Sulfated Dextran Beads for Isolation of Human Plasma Coagulation Factors II, IX, and $X^1$; Analytical Biochemistry 105:304–310.

Piszkiewicz, D. et al. (1989) "Virus Inactivation by Heat Treatment of Lyophilized Coagulation Factor Concentrates" Virus Inactivation in Plasma Products; Curr Stud Hematol Blood Transfus. Basel,Karger, 1989, No. 56, pp. 44–54.

Rubinstein, AiI. et al. (1991) "Combined Solvent–Detergent and 100° C. (Boiling) Sterilizing Dry–Heat Treatment of Factor VIII Concentrates to Assure Sterility" Vox Sang, 60:60.

Schilt, U. (1989) "Overview of Viruses Relevant to Blood Transfusion"; Virus Inactivation in Plasma Products; Curr Stud Hematol Blood Transfus. Basel,Karger, No. 56, pp. 1–8.

Winkelman, L. et al. (1989) "Severe Heat Treatment of Lyophilised Coagulation Factors"; Virus Inactivation in Plasma Products; Curr Stud Hematol Blood Transfus. Basel, Karger; No. 56, pp. 55–69.

*Primary Examiner*—Sandra E. Saucier
*Attorney, Agent, or Firm*—Mathews, Collins, Shepherd & Gould, P.A.

[57] ABSTRACT

This invention relates to a process for preparing biological glue components from a plasma pool which combines high recovery, quality product and viral safety. In first instance, a triple viral inactivated product comprising fibrogen, fibronectin and FXIII is obtained by treating a concentrate thereof first with a viricide solvent/detergent solution, second with viral nanofiltration, and third with heat. The recovery of a good quality product is not compromised by the process of the invention. In second instance, the same steps are reproduced for obtaining a triple viral safe thrombin product. In that case, a known proprietary process has been improved to increase the recovery of active thrombin by about two fold. One of the steps which increase the yield of thrombin is the dilution of the prothrombin solution with water 4 volumes to 1 volume prothrombin prior to acid precipitation.

37 Claims, 4 Drawing Sheets

PROCESS FOR PRODUCING THROMBIN FROM PLASMA

FIELD OF THE INVENTION

This invention is related to the production of highly viral safe biological glues composed of two components: a first one comprising coagulation protein concentrates, mainly fibrinogen, factor XIII and fibronectin, and a second one comprising thrombin concentrate from the same pooled human plasma. Particularly, this process involves three viral inactivation steps: solvent/detergent treatment, nanofiltration and heat treatment.

BACKGROUND OF THE INVENTION

The biological glues are adhesive protein concentrates composed of fibrin generated from fibrinogen activated by thrombin and factor XIII in presence of calcium ions. The adhesive power of blood clot, due to it network of polymerized fibrin, has been known for a long time. Fibrin has been used since the beginning of this century as an adhesive and discovered by Bergel in 1909 who recognized it as a physiological gluing substance and moreover ascribed it healing properties. This discovery was immediately followed by Grey's work in 1915 using fibrin tampons to stop brain, liver haemorrhages and in cerebral surgery. However, it is only in 1944 that Cronkite, then Tidrick and Warner used fibrinogen together with thrombin to secure skin graft. But the low concentration of these products did not allow a good quality adhesion nor a lasting effect. Since 1946, owing to important scientific research by E. J. Cohn on the fractionation of plasma proteins, coagulation proteins in particular have been used, and few years later the mechanism of coagulation and main coagulation proteins, notably factor XIII, were elucidated. In 1975, Matras was the first to use fibrin adhesive properties through highly concentrated fibrinogen. Since then, the biological glues have definitely supplanted the synthetic glues and are increasingly used in human clinical practice.

The biological glues introduce a new approach to surgeries and sutures. Surgeons have sought for a long time an effective, easy-to-use and above all easily tolerated adhesive that could be used in addition to or in replacement of sutures. Surgical sutures are important nowadays. However, numerous problems arise such as intolerance or toxicity. Blood, through its coagulation properties, has always represented for surgeons an ideal model of biological gluing but the use of biological glues prepared from human source raises a viral transmission problem. Virus transmission hazards depend greatly on the purification methods of plasma concentrates. For human clinical use, the biological glues must be prepared with the severe treatments for viral inactivation without affecting the quality of the products. Research is still under way to develop an adhesive combining the following properties:

high viral safety sufficient adhesivity good elasticity good hold on adjacent tissues absence of toxicity absence of metabolic action good tolerance The U.S. Pat. Nos. 5,290,918 and 5,395,923 issued to Haemacure Biotech Corp. described the methods of preparation and use of a concentrate of fibrinogen, Factor XIII and fibronectin for therapeutic purposes.

Because of its coagulation properties, the concentrate rich in fibrinogen and Factor XIII provides clinicians with a precious and effective tool for surgery, where haemostatic properties are greatly needed. The fields of clinical applications may be: neurosurgery, cardiovascular surgery, plastic surgery (skin graft), ORL surgery, stomatology, orthopedic surgery, general surgery and traumatology.

The main protein in this concentrate is fibrinogen which, through an enzymatic reaction in presence of thrombin and calcium ions, produces fibrinopeptides A and B permitting the formation of fibrin monomers. These monomers polymerize quickly and become soluble fibrin. Then, the fibrin stabilizing factor (Factor XIII), under the agency of calcium ions forms covalent bonds with the dissolved fibrin, which make it stable and insoluble in an acidic medium or in the presence of urea.

The fibrin thus formed is irreversible, stable and fully plays its role as coagulant. It resists fibrinolysis because of its high concentration, plasminogen free fibrinogen and keeps its shape as a result of the absence of exudation. This concentrate has the following characteristics: excellent stability after being dissolved again in a aqueous solution, solubilization at room temperature in a few minutes, good elasticity and, lastly, a good adhesion.

These characteristics depend only on the method of preparation from plasma. This is a simple, quick method easily adaptable to industrial production. All the concentrate biological and biochemical are preserved, and the product meets clinical requirements.

The use of blood-borne products always posed viral transmission problems despite available virological tests. The safest way to provide blood-borne safe products is to systematically inactivate viruses suspected to be present using appropriate techniques without deteriorating the biochemical properties of the plasma products. Numerous methods of viral inactivation based upon the nature of the viruses and the type of the proteins to be isolated are currently known, which is reflected by the increasing body of scientific publication in this respect.

The most widely used plasma products are albumin, immunoglobulins and concentrates of coagulation factors. In 1948, Gellis et al. were the first to use a method of inactivating viruses by heating an albumin preparation at 60° C. for ten hours. This method is currently used since that date due to its verified efficacy to reduce risks of viral transmission. The same method has been applied to the preparation of immunoglobulins G (IgG) with the same efficacy. This efficacy can be related to the method of purification of these blood products, particularly the use of a complete fractionation procedure as described by Cohn, or Kistler and Nitschmann.

The use of ethanol in numerous steps of fractionation of albumin and IgGs allows for a repartition of the quantity of viruses in different fractions. Ethanol is known as a disinfecting agent against pathogenic agents, such as viruses, as mentioned by Hénin et al. (1988) and Morgenthaler (1989).

Pasteurization of albumin and IgGs appeared at the beginning of the 50s. This technique, however, was directed to inactivation of hepatitis virus (hepatitis B and non A-non B). Curran et al. (1984) raised the issue of viral transmission of HIV type by transfusion or the use of other blood derivatives, particularly coagulation factors. Since then, methods of viral inactivation focused on HIV. No HIV transmission was signaled from the use of albumin or IgGs, this lack of viral transmission being assigned to the step of pasteurization (Mitra et al. (1986)). Coagulation factors such as factor VIII and IX are widely used by hemophilic patients.

Heimburger et al. (1980) have applied to these products the same pasteurization technique as described for albumin for inactivating viruses during the preparation of factor VIII in the presence of glycine and sucrose, in order to avoid proteic denaturation under thermal denaturation at 60° C. for ten hours. Their studies demonstrated the efficacy of inactivation of HIV, hepatitis B and hepatitis non A-non B. Hilfenhaus et al. (1985, 1986) confirmed that pasteurization is an efficient method for inactivating viruses such as HIV during the preparation of a concentrate of factor VIII. Tabor et al. (1982) inactivated hepatitis B virus by heating antithrombin III in the presence of citrate as a stabilizing agent. Hollinger et al. (1984) heated a concentrate of factor VIII in a lyophilized state for reducing the risk of transmission of HIV and hepatitis. Piszkiewicz et al. (1988) demonstrated that heat treatment of lyophilized concentrates of coagulation factors did not have any significant effect on the activity of these factors. These authors stressed that it was not obvious to find any production of neoantigens due to heat treatment. Studies on viral inactivation by heat treatment were conducted by Piszkiewicz et al. in preparations of "antihemophilic factors" (Hemofil® T, Hemofil® CT), wherein the latter were heated during 72 hours at 60° C., and during the preparation of anticoagulant inhibitor complexes (Autoplex® T), factor IX complex (Proplex® SX-T and Proplex®) T), wherein the latter were heated during 144 hours at 60° C. There has been no report on HIV seroconversion due to the use of any of the five heat-treated coagulation products. Hemofil® T concentrate made from plasma which has been screened of HBsAg and anti-HBc has been found not to transmit NANBH in a simian study. However, use of the same product made from plasma screened only for HBsAg resulted in NANBH in patients (Colombo et al. 1985). Hemofil® T is currently manufactured from plasma which is nonreactive for HBsAg and has normal ALT levels.

Viruses as well as proteins are more stable and more resistant to heat when in a dry state (lyophilized). The temperature and the duration of heating appear to vary upon the nature of the proteins to minimize denaturation thereof. However, the efficacy of viral inactivation have never been reported as perfect: NANBH transmission has been signaled by Colombo et al. HIV transmission has been reported by White et al. (1986) and Van den Berg et al. (1986). For these reasons, Winkelman et al. (1985) heated concentrate of factor VIII (type 8Y), factor IX (type 9A), factor VII, factor XI and thrombin at 80° C. for 72 hours. Studies conducted on 29 patients having received these heat-treated products have shown that there was no seroconversion of HIV of HB and that there was a significative reduction of the incidence of transmission of NANBH.

Other methods of viral inactivation have been developed using a light sources (UV, gamma rays, and laser) to irradiate the infectious agents in plasma. The following are cited as references: Oliphant et al.: Homologous serum jaundice: experimental inactivation of etiologic agent in serum by ultraviolet irradiation (Publ. Health Rep 1946; 61: 598–600), Wolf et al.: Ultraviolet irradiation of human plasma to control homologous serum jaundice (JAMA 1947; 135; 476477), Blanchard et al.: Methods of protection against homologous serum hepatitis. II. The inactivation of hepatitis virus serum with ultraviolet rays (JAMA 1948; 138:341), Murray et al. Effect of ultraviolet radiation on the infectivity of icterogenic plasma (JAMA 1955: 157: 8–14). Gurzadyan et al.: Mechanism of high power picosecond laser UV irradiation of viruses and bacterial plasmids (Photochem. Photobiol. 1981; 3: 835–838), Redfield et al.: Psoralen inactivation of influenza and herpes simplex virus and of viral infected cells (Infect Immun 1981; 32: 1216–1226), Heindrich et al.: Clinical evaluation of the hepatitis safety of beta-propiolactone-ultraviolet treated factor IX concentrate (PPBS), (Throm. Res. 1982; 28: 75), Kitchen et al.: Effect of gamma irradiation of the human immunodeficiency virus and human coagulation proteins (Vox Sang, 1989, 56: 233–229).

For more than ten years, one of the most currently used method for viral inactivation of viruses in blood-borne products is a method combining the use of a solvent and a detergent. This method has been developed by Neurath and Horowitz (U.S. Pat. No. 4,540,573 issued in September 1985, U.S. Pat. No. 4,613,501, U.S. Pat. No. 4,764,369 issued in August 1988; U.S. Pat. No. 4,820,805 issued in April 1989; U.S. Pat. No. 4,841,023 issued in June 1989 and U.S. Pat. No. 5,541,294 issued in July 1996). The mixture or solvent/detergent (Tri(n-butyl) phosphate/detergent) typically inactivates enveloped viruses such as HIV, HTLV-I, HBV and EBV.

Solvent/detergent method is however not sufficient to provide safe plasma products, because of the eventual presence of non-enveloped viruses such as parvovirus and poliovirus which are insensitive to solvent/detergent. Another technique has been recently introduced for eliminating non-enveloped viruses on which solvent/detergent has no effect. This technique is a nanofiltration. Nanofilters are composed with microporous fibers and have been commercialized under the name Planova BMM (Asahi Chemical Industries, Tokyo, Japan). The porosity of these filters varies from about 15 to 35 nm. These filters can retain certain types of viruses having a size larger than about 25 nm. These filters are efficient for eliminating viruses such as HIV-I (80–100 nm), HBB (42 nm), HCV (<80 nm), hepatitis Delta virus (35 nm), bovine viral diarrhea virus (60–70 nm), Sindbis virus (60–70 nm), reovirus type 3 (60–80 nm), poliovirus Sabin type 1(25–30 nm), human parvovirus (20–25 nm); Sekiguchi et al.: Possibility of hepatite B virus (HBV) removal from human plasma using regenerated cellulose hollow fiber (BMM) (Membrane, 1989; 14: 253–261), Hamamoto et al.: A novel method for removal of human immunodeficiency virus: filtration with porous polymeric membranes (Vox sang., 1989; 56: 230–236), Tsurumi et al.: Structure of cuprammonium regenerated cellulose hollow fiber (BMM hollow fiber) for virus removal (Polym. J. 1990, 22: 751–758), Ishikawa et al.: Novel determination method of size of virus in solution using cuprammonium regenerated cellulose membrane (BMM) (Membrane, 1991; 16:101–111), Tomokiyo et al.: Studies on virus elimination and inactivation effect of highly purified F-VIII concentrate (The clinical report, 1991; 25: 271–275), Manabe: Virus removal and inactivation in process validation (Animal Cell Technology: Basic & Applied Aspects (Murakami, H., Shirahata, S., Tachibana, H. eds, 1992, 15–30), Burnouf et al.: Strategy of virus removal/inactivation of plasma-derived products: Interest of nanofiltration as a new virus elimination method (manuscript submitted to JAACT 93).

Rubinstein et al. used a double viral inactivation of factor VIII concentrate by treating the latter with solvent/detergent and heating at 100° C. for 30 minutes the final product. Upon these authors, thermal treatment of the final product allows the inactivation of nonlipid-enveloped non A-non B hepatitis viruses. Heat treatment of the final product is also a cautious measure in case of accidental viral contamination during manipulation or due to the equipment (Vox Sang, 1991: 60: 60).

Recently, Proba et al. introduced a triple viral inactivation during the preparation of thrombin: (1) solvent/detergent treatment, (2) nanofiltration and (3) heat treatment at 100° C. for one hour of the lyophilized product (U.S. Pat. No. 5,506,127 issued to Haemacure Biotech Inc.).

The triple viral inactivation treatment confers an increased safety in the use of blood-borne products, particularly coagulation factors or biological glue.

Nobody has described a three viral inactivation step process for preparing a concentrate of other coagulation factors such as fibrinogen. Furthermore, the viral inactivation steps may also mean that the addition of numerous steps in a process of making blood-borne products will lead to a diminution of recovery of useful products. There is still room to improve recovery of blood-borne products and this, not at the expense of viral safety and product quality, or to improve product safety without sacrificing the recovery and nature of the product.

STATEMENT OF THE INVENTION

In accordance with the present invention is now provided a process of preparing biological glue components which combine high recovery, quality product and viral safety.

It is an object of the present invention to provide a method for preparing a protein concentrate coagulable by thrombin, substantially free of viral activity, which protein concentrate comprises proteins essentially consisting of fibrinogen, endogenous Factor XIII and fibronectin, which method comprises the following steps:

a) a precipitation effected on whole plasma proteins by the addition of a salt in a sufficient quantity to achieve a salting out effect and a pH of about 7.5 to about 8.5 at a temperature comprised between about 0° C. and 4° C., or to achieve an acidic precipitation at a pH of about 4.5 to about 5.5 at a temperature comprised between about 4° C. to about 20° C., whereby fibrinogen, Factor XIII and fibronectin are selectively precipitated proteins, said selective precipitation being conducted in the presence of a concentration of at least 50 mM of amino-6 hexanoic acid;

b) a solubilization of the precipitated proteins in the presence of about 0.2 to 0.3 g of L-Histidine per gram of proteins to form a solution containing the proteins;

c) a viral deactivation step of the solution obtained in step (b) in a viricide solvent-detergent solution;

d) adjusting the concentration of detergent to enable filtering of the solution on a filter of a porosity of about 35 nm without any substantial loss of said proteins;

e) filtering the solution obtained in d) on a filter of a porosity of about 35 nm; this step provides a second step of virus removal;

f) a precipitation of the filtered solution of step e) by the same salt as in step (a) at about the same temperature, in the presence of the about same concentration of amino-6 hexanoic acid to form a precipitate;

g) a washing of the precipitate of step f) to bring the washed precipitate to a neutral pH;

h) a solubilization of the washed precipitate of step g) in the presence of about 0.2 to 0.4 g of L-Histidine per gram of proteins;

i) an addition of protein stabilizer, the quantity of which is added with respect to the quantity of proteins obtained by step (h) to form a solution;

j) a sterile filtration of the solution obtained in step (i) to form a sterile filtered solution;

k) an aliquoting of the sterile filtered solution of step (j) in sterile bottles; and l) a lyophilization of the solution aliquoted in step (i) to provide a lyophilized concentrate.

To provide a triple viral inactivated product, the method further comprises a dry heat treatment of the lyophilized product at about 100° C. for about 1 to about 2 hours.

The viral deactivation of step c) is performed at about 24±1° C. during about six hours under continuous agitation in a solution consisting of about 10 mg/mL of solubilized proteins, 1% polyoxyethylene sorbitan monooleate and 0.3% Tri-n-butyl-phosphate (final concentrations).

Prior to the nanofiltration, polyoxyethylene sorbitan monooleate is adjusted to about 2% to 4%.

In a preferred embodiment, the precipitating salt is sodium or potassium acetate, or monobasic or dibasic sodium or potassium phosphate salt. Steps a) and f) are conducted for a period of time of at least about 30 minutes. Step (g) is performed at about 2° C. to about 20° C.

In a more preferred embodiment, g) further comprises (g.i) solubilizing the washed precipitate in pure water at neutral pH or basified to a pH of about 7.3; and (g.ii) dialyzing or diafiltering the solubilized precipitate of step (g.i); and in that step (h) further comprises adding the L-Histidine to the dialyzed or diafiltered precipitate to a final concentration of about 0.2 to 0.3 g of L-Histidine per gram of proteins.

The above-basified pure water used for solubilizing the precipitate before dialysis or diafiltration may be a solution of Tris 0.1 to 0.5% made in pure water.

In another embodiment, the precipitate of step g) is washed with a solution of Tris-HCl 0.1% of pH 4.5–5.0 or at pH 9.50–10.50 made in pure water.

The solubilization of step b) is preferably made in 1% Tris and 1.6% sodium citrate pH 6 to 7.3 or pH 9.5 to 10.5 to bring the protein concentration to about 20–22 mg/mL before adding L-Histidine.

The solubilization of step h) is preferably made in Tris 0.5% pH 6.8 to 7.3 to bring the protein concentration to 30–40 mg/mL before adding L-Histidine.

The protein stabilizer may comprise saccharose, albumin and polyoxyethylene sorbitan monooleate added to achieve a concentration of about 0.5 g/g protein, 0.05 g/g protein, and 17–20 μg/mg protein, respectively.

The lyophilized concentrate made by the method of this invention solubilizes in water in less than five minutes at room temperature under manual agitation to form a solubilized concentrate, and is stable at a temperature of about 4°–20° C. for at least 24 hours.

The whole plasma proteins used in step a) are of human or of animal origin.

It is another object of the invention to provide a process for the large-scale production of a storage-stable therapeutic grade thrombin composition substantially free from active viruses, comprising the steps of:

a) recovering the supernatant obtained from step a) of the method of claim 1;

b) diafiltering said supernatant against an exchanged low or free salt solution;

c) diluting said diafiltered supernatant until the obtention of a prothrombin solution of about 100 mosmoles/kg of weight or lower;

d) precipitating prothrombin by adding an acidic solution until a pH of about 5.2 is obtained;

e) solubilizing the precipitate of step d) in a solution having a near neutral pH;

f) converting the prothrombin of step e) into thrombin in the presence of a diluting solution of calcium chloride to achieve a concentration of calcium chloride of about 20 to about 30 mM;

g) incubating said thrombin with a viricide solvent/detergent solution in an amount sufficient to inactivate lipid-containing viruses;

h) purifying the incubated material by sequential ion-exchange chromatography using a single sulfalkyl-activated polysaccharide cation exchange medium selected from the group consisting of a sulfakyl-activated polyagarose, a sulfakyl-activated polydextran and a noncompressible composite medium of sulfalkyl-activated dextran and silica particles having a high selectivity for thrombin using as an eluting agent at least three and increasing concentrations of an aqueous buffer solution; and i) recovering thrombin peak eluate from the chromatography of h) and exchanging the buffer of the eluate with a physiologically compatible stabilizing formulation buffer for stabilizing the recovered thrombin and recovering a formulation buffer solution of thrombin.

In a preferred embodiment, step b) comprises exchanging a water solution in a volume equivalent to about four fold the volume of supernatant.

In a more preferred embodiment, the diluting solution of step f) is a calcium chloride 40 mM added in a volume equivalent to about four fold the volume of the solubilized precipitate of step e).

The cation exchange medium is said non-compressible composite medium of sulfoalkyl-activated dextran and silica particles.

Preferably, the sulfolalkyl-activated dextran is sulfopropyl-activated dextran and silica particles. The increasing buffer concentrations consist essentially of about 0.08M, 0.15M and 0.4M NaCl buffer for human thrombin.

In still a preferred embodiment, the method further includes filtering the thrombin formulation buffer solution over a hollow fiber cuprammonium cellulose membrane to filter out virions present in the formulation buffer solution, and recovering a substantially virion-free formulation buffer solution of thrombin.

The hollow fiber cuprammonium cellulose membrane has preferably a porosity of about 15 nm.

In still a more preferred embodiment, the method further includes lyophilization and dry heat treatment of the thrombin formulation buffer solution after filtration to inactivate any remaining virions without denaturation of thrombin.

Preferably, the dry heat treatment is achieved by heating the lyophilized product for about 1 to about 2 hours at about 100° C.

The formulation buffer solution may comprise an aqueous solution of citrate salt, sodium chloride, Tris-HCl, and serum albumin at a pH of about 7.3, in amounts sufficient to stabilize the thrombin against substantial loss of activity during heat treatment.

In a specific embodiment, the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

The advantage of the present invention is to meet all the industrial requirements of cost-effectiveness and viral safety.

DESCRIPTION OF THE INVENTION

This invention will be described hereinbelow with reference to the following specific examples and drawings, which purpose is to illustrate the invention and not to limit its scope.

EXAMPLE 1

Figure 1A:
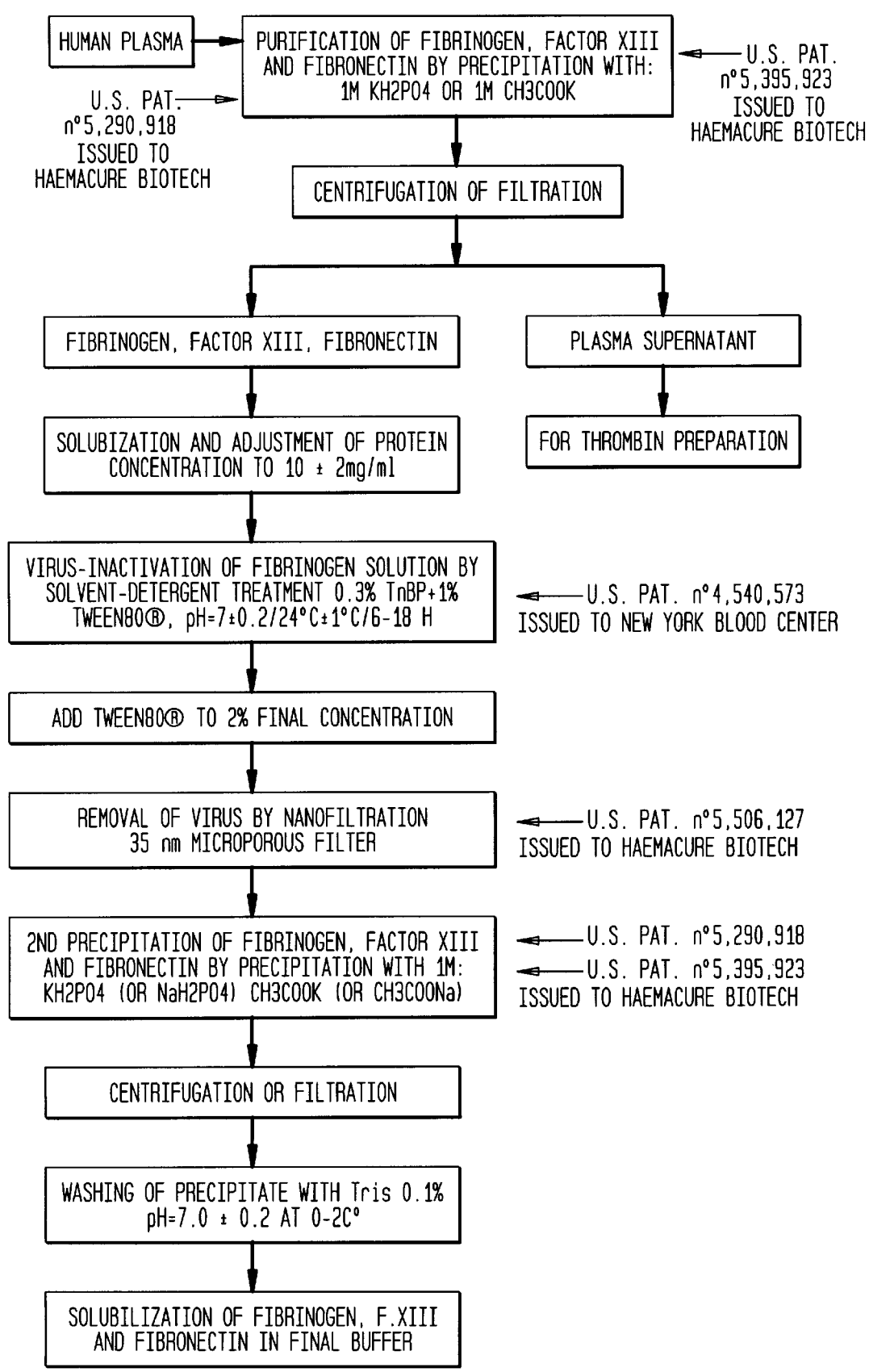
FIG. 1 illustrates the steps of preparation of a concentrate of fibrinogen, factor XIII and fibronectin, starting from a human plasma pool, in accordance with the present invention.

Preparation of a Concentrate Rich in Fibrinogen, Factor XIII and Fibronectin:

First fractionation

The pool of plasma is maintained at a temperature comprised between about 16 and about 37° C. Amino-6-hexanoic acid is added under agitation to achieve a minimal concentration of 50 mM. The mixture is incubated for at least 15 minutes at 35 to 37° C. The mixture is then cooled down to 0° C.±2° C. Sodium or potassium phosphate monobasic (U.S. Pat. No. 5,290,918, issued to Haemacure Biotech Inc.) or sodium or potassium acetate (U.S. Pat. No. 5,395,923, issued to Haemacure Biotech Inc.) is added to achieve a final concentration of 1M. The mixture is agitated during about 0.5 to 1 hour at about 0° to 4° C.±2° C. Acidic precipitation with phosphates may also be performed at room temperature (about 20° C.).

Centrifugation:

The mixture is filtered or centrifuged at 4,200 rpm (Beckman J6-MC, rotor 4.2 type) during 20 minutes at 4° C. The supernatant is recovered for thrombin preparation and the precipitate is transferred into another beaker. The supernatant may be used immediately for further processing or conserved at a temperature inferior to −30° C., preferably at −80° C. for many months or at 2° to 4° C. for about 24 hours.

Solubilization:

The precipitate obtained, rich in fibrinogen, factor XIII and fibronectin, is solubilized with a buffer containing 1% Tris and 1.6% sodium citrate pH: 6.0±0.1 (pH 7.3 also works). The precipitate is solubilized at room temperature, under agitation. The buffer described above is added as needed to get a protein concentration of about 20–22 mg/mi. At this point, L-Histidine is added at the rate of 0.2–0.3 g per gram of protein. The protein solution is then centrifuged at 10,000 rpm for 20 minutes at about 4° C. (Beckman J2-MI, rotor JA-10 type). A lipid layer floating at the surface of the protein solution is removed. The protein solution is gently transferred into a beaker and filtered through a 0.2 micron capsule filter (Gelman SuporCap, product No. 12991 or 12992).

Solvent/detergent treatment

The protein solution thus filtered is submitted to a virus inactivation treatment by mixing with an equal volume of a solution containing 1% Tris, 1.6% sodium citrate, 2% Tween80® (polyoxyethylene sorbitan monooleate) and 0.6% Tris n-butyl-phosphate (TnBP), pH: 6.8±0.1. This brings the final concentration to about 10 mg/ml protein, 1% Tween80® and 0.3% TnBP, the final pH is about 7.0±0.2. The solution is incubated at 24° C.±1° C., under constant agitation for at least a 6 hour period.

Virus removal by nanofiltration:

After the virus inactivation treatment, the Tween80® in the protein is then adjusted to 2% to 4% final concentration with a buffer containing 1% Tris, 1.6% sodium citrate, Tween80® 6%, pH: 7.0±0.1. The mixture is then filtered through cascade capsule filters 0.2 and 0.1 micron (Gelman CritiCap 0.2 μ, product No. 12995 or 12996; CritiCap 0.1 μ product No. 12997 or 12999) and the filtered solution is passed through the Planova BMM filter 35 nm. Addition of Tween80® is necessary to facilitate the filtration of a high molecular weight molecule like fibrinogen and to optimize its recovery. In absence of Tween 80™, the filter becomes rapidly blocked because of the proteic load.

Second fractionation:

A quantity of 50 mM amino-6 hexanoic acid is added to the filtrate under agitation and the mixture is incubated at 35° C.±2° C. for about one hour and then cooled down to 0° C.±2° C. A quantity of sodium or potassium phosphate monobasic (U.S. Pat. No. 5,290,918 issued to Haemacure Biotech Inc.); or of sodium or potassium acetate (U.S. Pat. No. 5,395,923 issued to Haemacure Biotech Inc.) equivalent to one mole per liter of mixture is added, and the precipitate appears instantaneously. Agitation continues for one hour at 0° C.±2° C.

Centrifugation:

The mixture is filtered or centrifuged at 4,200 rmp (Beckman J6-MC, rotor 4.2 type) for 20 minutes at 4° C. The solvent, the detergent and the contaminating proteins are eliminated by centrifugation. The precipitate is recovered and transferred into a beaker.

Washing:

The precipitate is washed several times (at least 2 times) with a 0.1% Tris, pH: 7.0±0.1 buffer. Depending on the salt used in the previous precipitation step, the pH and concentration of the Tris solution may vary from 4.5–5.0 to 9.5–10.5 (concentration of 0.1 to 0.5%) to neutralize the solution. The precipitate is separated by centrifugation after every washing step. The Tris buffer is precooled at 0° C.±2° C. and the washing steps are carried out at 0° C.±2° C. Working at room temperature also achieves good results. The number of washing steps may be decreased by performing a simple dialysis or a diafiltration after the precipitate is put back into final buffer, using a water solution basified to pH 7.3.

Solubilization:

The washed precipitate is dissolved in a final buffer containing 0.5% Tris, 0.1% NaCl and 0.5% sodium citrate, pH: 6.8±0.1 (pH 7.3 also works). The volume of buffer is about 2 to 3 ml/g of weighed precipitate. The solubilization of precipitate may be accelerated by heating at 37° C. After complete solubilization, a quantity of L-Histidine corresponding to 0.2–0.3 g per liter of starting plasma is added. The protein solution is then filtered or centrifuged at 10,000 rpm for 20 minutes at about 4° C. (Beckman J2-MI, rotor JA-10 type).

Figure 1B:
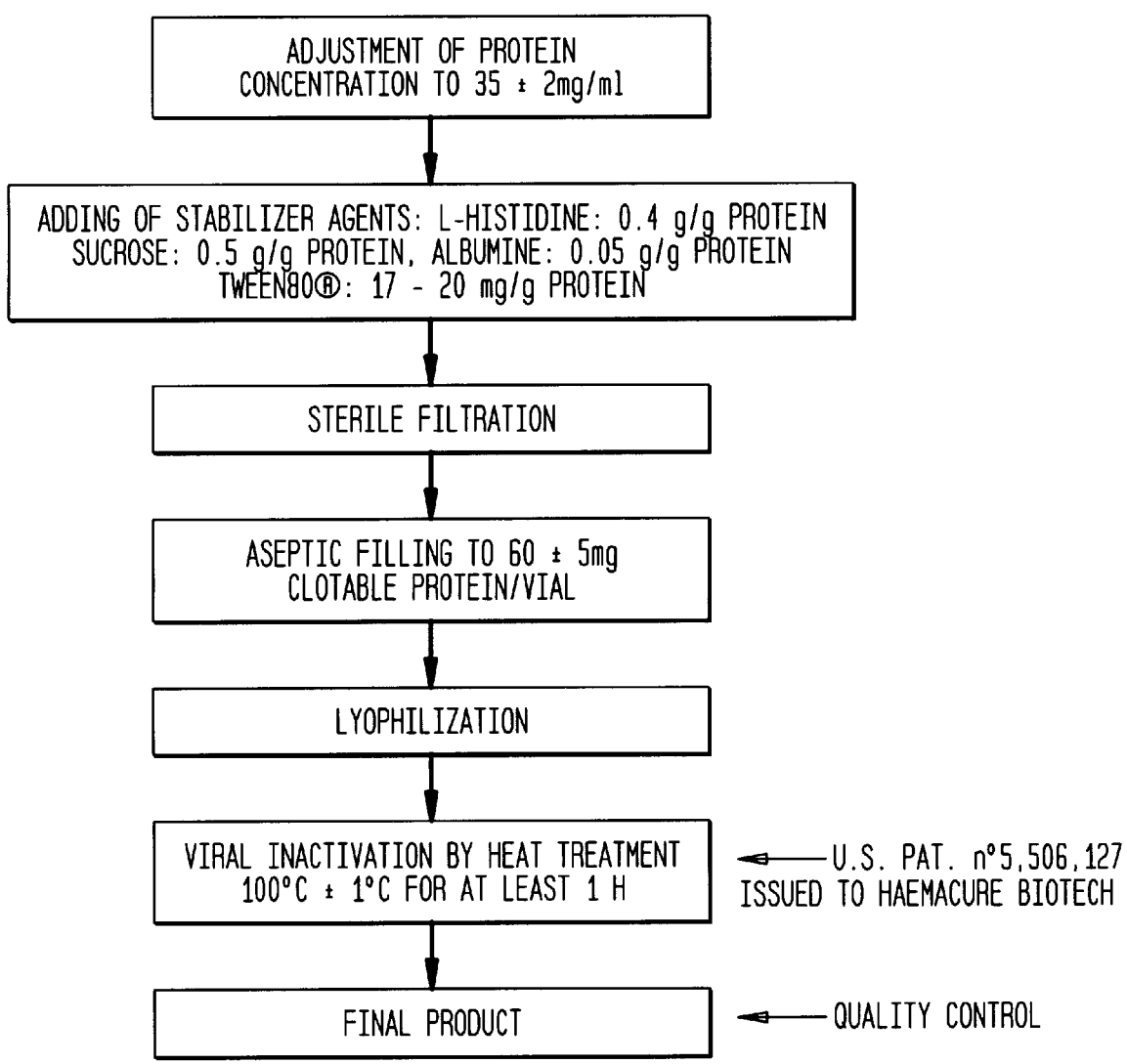

The FIG. 1 shows the final steps of the preparation of a concentrate rich in fibronectin, Factor XIII and fibronectin.

Adjustment of protein concentration:

The final protein concentration is adjusted to around 30–40 mg/ml with the same buffer. The protein concentration is measured par O.D. 280 nm.

Formulation:

A final concentration of L-Histidine is adjusted to 0.2–0.4, preferably 0.4 g per gram of protein, measured by O.D. according to the following formula:

[0.4 g )L-Histidine)xprotein concentration mg/ml (O.D.)xvolume]−Added L-Histidine 0.2–0.3 g/L plasma]

A quantity of saccharose corresponding to 0.5 g/g of protein measured by O.D. is added into the mixture.

A quantity of human albumin (25% in solution, approved for human use Plasbumin 25® from Miles Inc. Pharmaceutical Division, Indiana 46515 USA) corresponding to 0.2 ml/g of protein measured by O.D. is added to the mixture.

A quantity of Tween80® is adjusted to 17–20 μg/mg of protein measured by O.D. with the buffer containing 0.5% Tris, 0.1% NaCl, 0.5% sodium citrate and 10% Tween80®, pH: 6.8±0.1. The Tween80® must be verified by O.D. 620 nm before adjusting according to New York Blood Center's technique.

Sterile filtration:

The final protein solution is filtered through a 0.2 micron capsule filter (Gelman, CritiCap 0.2 μ, product No. 12995 or 12996).

Aseptic filling:

The protein solution is filled into 10 ml vials at the rate of 60±5 mg of clotable fibrinogen per vial.

Lyophilization:

Flasks containing 60±5 mg of coagulable fibrinogen are submitted to lyophilization for 66–72 hours. Temperature progressively increases from −40° C. to 22° C.±2° C. (the slope of increase was 0.02° C. per minute). This lyophilization step confers to the product a residual moisture inferior to 1 %, avoiding product denaturation during further heat treatment.

Dry heating:

After lyophilization cycle, the vials are closed under vacuum with stoppers and sealed with aluminium caps. The vials are then submitted to the third virus inactivation by dry heat treatment at about 100° C.±1° C. for 1 to 2 hours according to the process disclosed U.S. Pat. No. 5,506,127 issued in Apr. 1996.

Viral safety:

Viral safety was assessed. Small non-enveloped viruses like parvovirus, poliovirus and hepatitis A virus are inactivated during heat treatment. A major expectable problem of recovery was to obtain the best possible quantity of fibrinogen after nanofiltration. This difficulty has been obviated by properly adjusting the Tween80® concentration to favorize the passage of fibrinogen through the nanofilter. Non-enveloped viruses reovirus 3 and SV40 have been removed by nanofiltration. Therefore, each viral inactivation step achieved its purpose: removing or inactivating viruses at each adequate step, providing a viral safe product. This means that combination of three steps insures inactivation or capture of viruses through at least one of them; otherwise viruses resistant to one or two steps can be retrieved in the final product.

Recovery:

The overall recovery of fibrinogen, fibronectin and Factor XIII is equivalent to the one reported in U.S. Pat. No. 5,290,918 and 5,395,923, meaning that viral safety is insured while preserving the activity of the proteins.

Thrombin

Reducing salt content by diafiltration:

The plasma supernatant obtained after a first centrifugation of a acid or salting out precipitation of plasma (as in Example 1) contains an important quantity of salts. Plasmatic osmolarity upon treatment with salts is comprised between about 2,200 and 2,500 mosm/kg. This high quantity of salt should be removed in order to isolate the prothrombin present in that supernatant. Isolation of prothrombin can be realized only when the plasmatic medium has a low ionic strength, particularly when a acid precipitation has been used. Removal of salt is made by the classical diafiltration technique. The supernatant is transferred in a diafiltration system reservoir (Amicon system, model DC10L with spiral cartridge). Diafiltration is achieved against pure water. One volume of plasma supernatant is exchanged for an average of four volumes of pure water or until the plasma osmolarity is below about 50 to 100 mOsm/kg.

Prothrombin recovery:

Diafiltered plasma is five-fold diluted with pure water. The pH of the diluted plasma is comprised between about 7.4–7.8. The pH is lowered to 5.2±0.1 by dropwise addition of an acetic acid solution (2 to 5%; Allary et al. Ann. pharmaceutiques francaises 48, 129–135, 1990). Prothrombin precipitates during pH lowering (at about 5.5–6.0) and is completely precipitated at a pH comprised between 5.1 to 5.3. Prothrombin is rapidly resolubilized at pH higher than 6.0 and by increasing salt concentration. Plasma is incubated with no agitation for one hour at room temperature and further centrifuged at 4,200 rpm for 20 minutes at 20° C. (Beckman J6MC, rotor JS 4.2). The precipitate is recovered and solubilized in a Tris—HCl 2% buffer solution at pH 7.5±0.1 (volume: 120–150 ml per liter of plasma supernatant). The quantity of prothrombin is determined by chronometric dosage (Fibromètre Stago ST4—France). The recovery of prothrombin is about 90% with regard to the plasma supernatant and the starting plasma, which provides about 750 to 850 units prothrombin per liter of plasma.

Conversion of prothrombin into thrombin:

Four volumes of $CaCl_2$ 40 mM are rapidly added to one volume of prothrombin solution under agitation for a few minutes. The mixture is incubated at room temperature for about one hour or more and centrifuged at 4,200 rpm for 30 minutes at 20° C. (Beckman centrifuge J6MC, rotor JS 4.2). The supernatant containing thrombin is recovered and filtered on 0.2 micron filter (Gelman SuporCap, product No. 12991 or 12992). Activity of the crude thrombin obtained after conversion of prothrombin is about 110 to 120 NIH units/ml. The specific activity is about 25 to 30 NIH units/mg of protein, or 80 to 100 NIH units of thrombin per unit of prothrombin. The global recovery of thrombin is approximately of 60,000–80,000 NIH units per liter of plasma supernatant, e.g. twice as much as the recovery measured with the process described in U.S. Pat. No. 5,506,127.

Thrombin activity was evaluated by measuring the coagulation time on fibrometer (Fibromètre Stago ST4—France) and expressed in NIH units. The standard curve has been established with thrombozyme (Stago reagents, Thrombozyme ref. 00332); the activity of the latter has been determined from a NIH standard, lot J (titer 310 NIH). The pool of plasma was used as a fibrinogen source for determining thrombin activity.

Figure 2A:
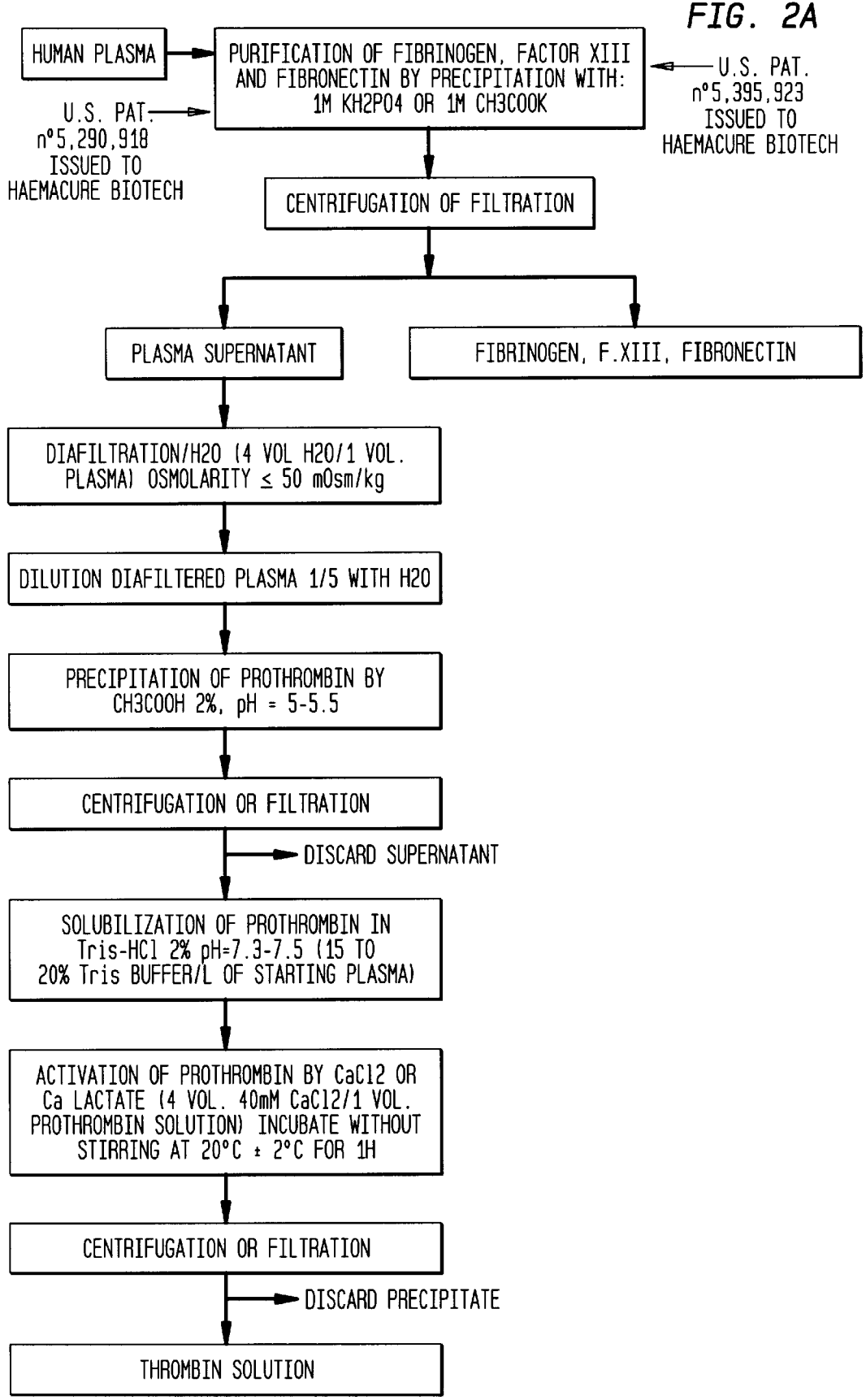
FIG. 2 shows a process of preparation of thrombin starting from a plasma supernatant left during the isolation of a concentrate of fibrinogen, factor XIII and fibronectin, in accordance with the present invention.
Figure 2B:
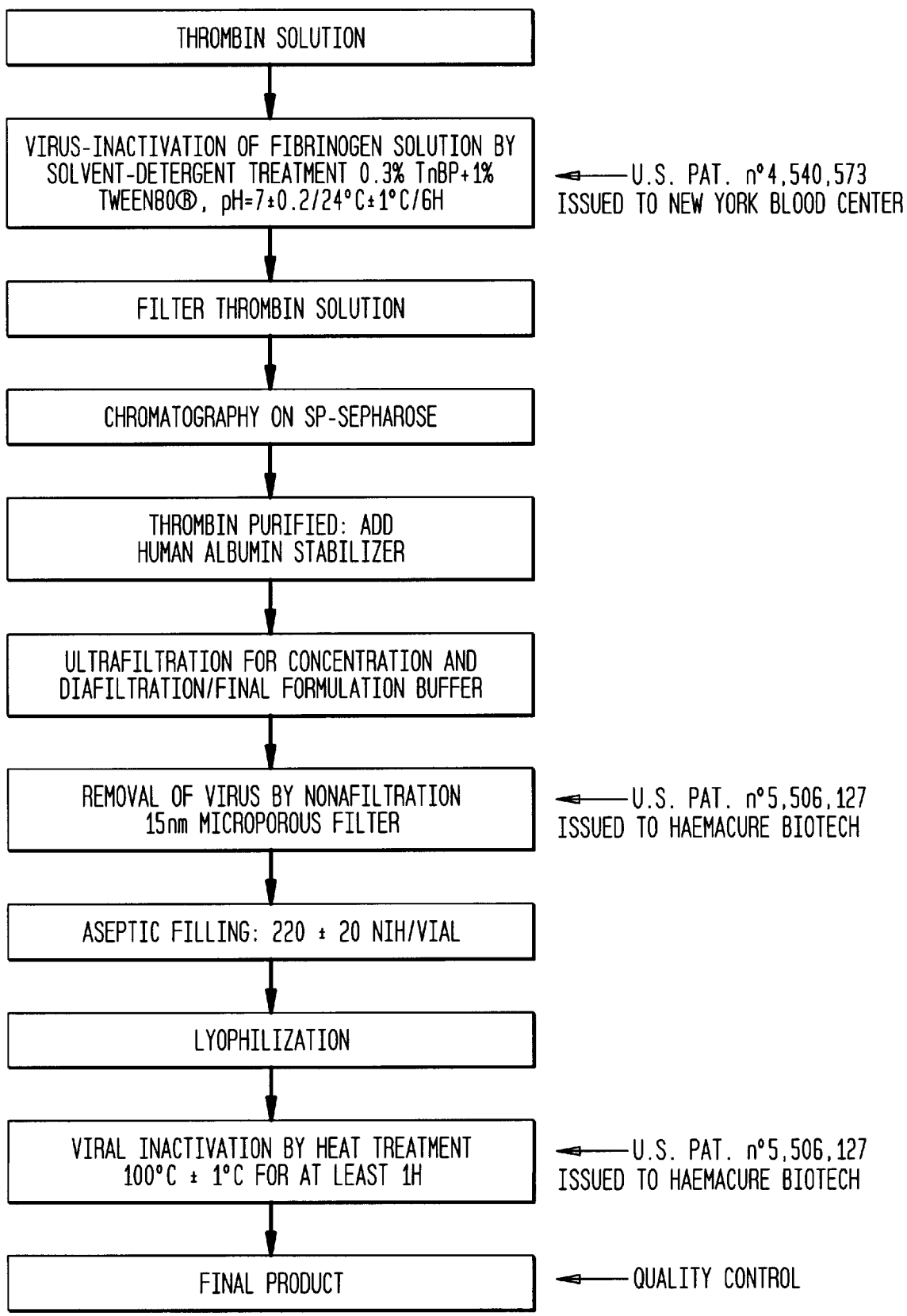

Viral inactivation by solvent/detergent:

FIG. 2 shows the steps of viral inactivation performed on a thrombin solution by successively treating the latter with a solvent/detergent technique, purifying thrombin by chromatography, viral filtration, formulation, lyophilization and heat viral inactivation at 100° C. Thrombin solution is transferred into double-wall tank equipped with a thermostated liquid circulation system at 24° C±0.5° C. Solution comprising 11% Tween80® and 3.3% Tri-n-butyl phosphate (TnBP) prepared in Tris 0.5%, pH 7.0±0.1, is added to the thrombin solution under mild agitation. The volume of solvent/detergent represents one tenth of the volume of the thrombin solution. After one hour agitation, the mixture is transferred into a second tank similar to first and the agitation is continued for an additional period of time of about 5 hours. Thrombin activity measured after viral inactivation shows that there was no significant loss of activity during the solvent/detergent treatment (0 to 5%). It is worthwhile noting that if a quantity of solid $CaCl_2$ about equivalent to the quantity of liquid $CaCl_2$ was added to convert prothrombin into thrombin, recovery was lowered by 20% in the case of the powder and a loss of activity of about 10 to 15% occurred during solvent/detergent treatment. The overall difference between adding calcium powder vs $CaCl_2$ solution represents a loss of about 30% of thrombin activity for the former.

Purification of thrombin by chromatography:

Thrombin is further purified during a one single cation-exchange chromatography step. Purification of proteins by chromatography is well known and described in details in many references. The use of different matrices or supports is a function of the purification objective and of the nature of the proteins. In the present case, the support is a rigid agarose gel comprising a grafted sulphopropyl ($—CH_2—CH_2—CH_2—SO_3$) moiety. Gel named SP Sepharose Fast Flow™ (Pharmacia, code No. 17-0729-01) is a strong cation exchanger with excellent flow properties and high capacity for proteins of all pI values. The ion exchange group is sulphopropyl which remains charged and maintain consistently high capacities over the entire working range, at pH 4–13. The proteic solution comprising crude thrombin is passed through a SP Sepharose containing column. Thrombin and contaminating proteins are adsorbed on the support. Extensive washing of the gel with a solution NaCl 0.08 M is necessary before eluting proteins retained on the gel. Elution of thrombin is effected in a discontinuous NaCl gradient. A 0.15 M NaCl solution is first passed through the column to remove contaminating proteins. Thrombin is completely deadsorbed and recovered in NaCl 0.4 M. The gel is then rid of all adsorbed impurities by washing with a solution of NaCl 2 M. Purification of thrombin by chromatography also allows removal of solvent/detergent used in the previous viral inactivation step. The purified thrombin solution is stabilized by adding human albumin (human albumin solution 25%-USP Plasbumin-25, Miles Inc. Pharmaceutical Division, Indiana 46515 USA). Quantity of albumin to be added is calculated upon the following formula:

$$\frac{20 \times [c]\text{thrombin(measured/ O.D.)} \times \text{thrombin volume(after chromatography)} \times 100\,\text{ml}}{25 \times 1000}$$

Thrombin in solution after chromatography purification is very unstable. A loss of activity may be important if thrombin is not preserved rapidly at low temperature or if other steps such as diafiltration and concentration are undertaken without stabilization. The use of a stabilizer such as albumin is essential to protect the thrombin activity during a buffer exchange for a final formulation (Amicon system CH2PRS or TCF 10 upon the volume). The final formulation is in a buffer comprising 0.25% Tris—0.25% sodium citrate—0.45% NaCl, pH 7.30±0.1. About six volumes of formulation buffer are exchanged for one volume of thrombin solution. Thrombin solution may be concentrated several folds before diafiltration for diminishing the volume to be exchanged and reducing the diafiltration time.

Viral filtration:

In accordance with the teachings of U.S. Pat. No. 5,506,127 issued on Apr. 9, 1996, the diafiltered thrombin solution is then filtered over a hollow-fiber membrane such as a Planova BMM microporous membrane (Bemberg microporous membrane BMM Development, Asahi Chemical Industries, Tokyo, Japan) comprising a cuprammonium regenerated cellulose fiber having a pore size of about 15 nm. This technique substantially allows the remove non-lipid-enveloped viruses which cannot be inactivated by SD treatment of the process.

Aseptic filling:

Thrombin solution after nanofiltration is diluted to about 250 NIH units/ml and aliquoted in 5 ml glass flasks.

Lyophilization:

The flasks containing 1 ml of thrombin solution are lyophilized for 66 to 72 hours. The temperature progressively increases from −40 to 22±2° C. with a temperature increasing rate of about 0.02° C. per minute. This step achieves a residual moisture content inferior to 1%.

Dry heating:

After lyophilization cycle, the vials are closed under vacuum with stoppers and sealed with aluminium caps. The vials are then submitted to the third virus inactivation by dry heat treatment at about 100° C.±1° C. for about 1 to 2 hours.

Conclusion:

Starting from the methods taught in U.S. Pat. No. 5,290,918, U.S. Pat. No. 5,395,923 and U.S. Pat. No. 5,506,127, all granted the Haemacure Biotech Inc, the present invention has demonstrated that these methods can be improved to increase the recovery of thrombin having a great degree of safety, and to insure the viral safety of a fibrinogen concentrate without sacrificing recovery.

This invention has been described hereinbelow, and it will readily be apparent to the skilled artisan that modifications can be made to the preferred embodiments without departing from the teachings and spirit of the invention. These modifications are under the scope of the invention as defined in the appended claims.

What is claimed is:

1. A process for the production of thrombin, comprising the steps of:
   a) precipitating whole plasma proteins by the addition of a first salt in a sufficient quantity to achieve a salting out effect and a pH of about 7.5 to about 8.5 at a temperature comprised between about 0° C. and about 4° C., or by the addition of a second salt in sufficient quantity to achieve an acidic precipitation at a pH of about 4.5 to about 5.5 at a temperature comprised between about 4° C. to about 20° C., whereby fibrinogen, Factor XIII and fibronectin are precipitated, said precipitation being conducted in the presence of a concentration of at least 50 mM of amino-6 hexanoic acid, and recovering the supernatant which comprises pro-thrombin;
   b) diafiltering said supernatant until a pro-thrombin solution which has an osmolarity of about 100 mosmoles/kg of weight or lower is obtained;
   c) diluting said pro-thrombin solution with water which is added in a ratio of about 4 volumes to 1 volume of the prothrombin solution;
   d) precipitating prothrombin by adding an acidic solution until a pH of about 5.2 is obtained;
   e) solubilizing the precipitate of step d) in a solution having a near neutral pH; and
   f) converting the prothrombin of step e) into thrombin in the presence of calcium chloride to achieve a concentration of calcium chloride of about 20 to about 32 mM;
   g) incubating said thrombin with a viricide solvent/detergent solution in an amount sufficient to inactivate lipid-containing viruses;
   h) purifying the incubated thrombin by a sequential ion-exchange chromatography using a single sulfalkyl-activated polysaccharide cation exchange medium selected from the group consisting of a sulfakyl-activated polyagarose, a sulfakyl-activated polydextran, and a noncompressible composite medium of sulfalkyl-activated dextran and silica particles having a high selectivity for thrombin using as an eluting agent at least three and increasing concentrations of an aqueous salt solution; and
   (i) recovering a thrombin peak eluate from the chromatography of h) and exchanging the salt of the eluate with a physiologically compatible stabilizing formulation buffer for stabilizing the recovered thrombin and recovering a formulation buffer solution of thrombin.

2. The method according to claim 1 wherein the diafiltering step b) comprises exchanging water in a volume which is equivalent to about four times the volume of supernatant.

3. The method according to claim 1, wherein in step f), calcium chloride is added as a solution of about 40 mM in a ratio of about 4 volumes to 1 volume of the solubilized precipitate of step e).

4. The process according to claim 1, which further comprises the following steps:
   g) incubating said thrombin with a viricide solvent/detergent solution in an amount sufficient to inactivate lipid-containing viruses;
   h) purifying the incubated thrombin by sequential ion-exchange chromatography using a single sulfalkyl-activated polysaccharide cation exchange medium selected from the group consisting of a sulfakyl-activated polyagarose, a sulfakyl-activated polydextran and a noncompressible composite medium of sulfalkyl-activated dextran and silica particles having a high selectivity for thrombin using as an eluting agent at least three and increasing concentrations of an aqueous salt solution; and
   i) recovering a thrombin peak eluate from the chromatography of h) and exchanging the salt of the eluate with a physiologically compatible stabilizing formulation buffer for stabilizing the recovered thrombin and recovering a formulation buffer solution of thrombin.

5.) The method according to claim 4, wherein in step f) calcium chloride is added as a solution of about 40 mM in a ratio of about 4 volumes to 1 volume of the solubilized precipitate of step e).

6. The process of claim 5, further including step j): filtering the thrombin formulation buffer solution over a hollow fiber cuprammonium cellulose membrane to filter out virions present in the formulation buffer solution, and recovering a substantially virion-free formulation buffer solution of thrombin.

7. A process according to claim 6, wherein said hollow fiber cuprammonium cellulose membrane has a porosity of about 15 nm.

8. The process of claim 7, further including the following steps:
   k) lyophilizing the solution of thrombin obtained from step j): and
   l) dry heating the lyophilized thrombin formulation to inactivate any remaining virions without denaturation of thrombin.

9. The process according to claim 8 wherein said the step of dry heating is achieved by heating the lyophilized product for about 1 to about 2 hours at about 100° C.

10. The process of claim 9, wherein the formulation buffer solution comprises an aqueous solution of citrate salt, sodium chloride, Tris-HCl, and serum albumin a pH of about 7.3, in amounts sufficient to stabilize the thrombin against substantial loss of activity during heat treatment.

11. The process of claim 10, wherein the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

12. The process of claim 11, wherein the cation exchange medium is a substantially non-compressible composite medium of sulfoalkyl-activated dextran and silica particles.

13. The process of claim 12, wherein the cation exchange medium is a substantially non-compressible composite medium of sulfopropyl-activated dextran and silica particles.

14. The process according to claim 5, wherein the cation exchange medium is a substantially non-compressible composite medium of sulfoalkyl-activated dextran and silica particles.

15. The process of claim 14, wherein the cation exchange medium is a substantially non-compressible composite medium of sulfopropyl-activated dextran and silica particles.

16. The method of claim 15, wherein said at least three and increasing salt concentrations of an aqueous salt solution consist essentially of about 0.08M, 0.15M and 0.4M NaCl buffer for human thrombin.

17. The process of claim 6, further including the following steps:
   k) lyophilizing the solution of thrombin obtained from step j): and
   l) dry heating the lyophilized thrombin formulation to inactivate any remaining virions without denaturation of thrombin.

18. The process of claim 17, wherein the formulation buffer solution comprises an aqueous solution of citrate salt, sodium chloride, Tris-HCl, and serum albumin at a pH of about 7.3, in amounts sufficient to stabilize the thrombin against substantial loss of activity during heat treatment.

19. The process of claim 18, wherein the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

20. The process according to claim 17 wherein said the step of dry heating is achieved by heating the lyophilized product for about 1 to about 2 hours at about 100° C.

21. The method according to claim 7, wherein the incubating step g) is conducted in the presence of a viricide solvent/detergent solution that is free of sodium citrate.

22. The process of claim 8, wherein the formulation buffer solution comprises an aqueous solution of citrate salt, sodium chloride, Tris-HCl, and serum albumin at a pH of about 7.3, in amounts sufficient to stabilize the thrombin against substantial loss of activity during heat treatment.

23. The process of claim 22, wherein the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

24. The method according to claim 8, wherein the incubating step g) is conducted in the presence of a viricide solvent/detergent solution that is free of sodium citrate.

25. The method according to claim 11, wherein the incubating step g) is conducted in the presence of a viricide solvent/detergent solution that is free of sodium citrate.

26. The method of claim 12, wherein said at least three and increasing salt concentrations of an aqueous salt solution consist essentially of about 0.08M, 0.15M and 0.4M NaCl buffer for human thrombin.

27. The process according to claim 5, wherein the cation exchange medium is a substantially non-compressible composite medium of sulfoalkyl-activated dextran and silica particles.

28. The process of claim 27, wherein the cation exchange medium is a substantially non-compressible composite medium of sulfopropyl-activated dextran and silica particles.

29. The method of claim 28, wherein said at least three and increasing salt concentrations of an aqueous salt solution consist essentially of about 0.08M, 0.15M and 0.4M NaCl buffer for human thrombin.

30. The process of claim 4, further including step j): filtering the thrombin formulation buffer solution over a hollow fiber cuprammonium cellulose membrane to filter out virions present in the formulation buffer solution, and recovering a substantially virion-free formulation buffer solution of thrombin.

31. The process of claim 30, further including the following steps:
   k) lyophilizing the solution of thrombin obtained from step j): and
   l) dry heating the lyophilized thrombin formulation to inactivate any remaining virions without denaturation of thrombin.

32. The process of claim 31, wherein the formulation buffer solution comprises an aqueous solution of citrate salt, sodium chloride, Tris-HCl, and serum albumin at a pH of about 7.3, in amounts sufficient to stabilize the thrombin against substantial loss of activity during heat treatment.

33. The process of claim 32, wherein the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

34. A process according to claim 30, wherein said hollow fiber cuprammonium cellulose membrane has a porosity of about 15 nm.

35. The process according to claim 31 wherein said the step of dry heating is achieved by heating the lyophilized product for about 1 to about 2 hours at about 100° C.

36. The method according to claim 4, wherein said at least three and increasing salt concentrations of an aqueous salt solution consist essentially of about 0.08M, 0.15M and 0.4M NaCl buffer for human thrombin.

37. The method according to claim 4, wherein the incubating step g) is conducted in the presence of a viricide solvent/detergent solution that is free of sodium citrate.

* * * * *